United States Patent [19]

Conrad

[11] 4,106,263
[45] Aug. 15, 1978

[54] APPARATUS FOR PRESSURE TESTING OF CONTAINERS

[75] Inventor: William A. Conrad, Pinole, Calif.

[73] Assignee: Rheem Manufacturing Company, New York, N.Y.

[21] Appl. No.: 816,654

[22] Filed: Jul. 18, 1977

[51] Int. Cl.² .................. B65B 31/02; G01M 3/32
[52] U.S. Cl. ........................... 53/97; 73/37; 73/49.2
[58] Field of Search ............. 73/49.2, 49.3, 37, 45.5; 226/82; 53/7, 86, 97

[56] References Cited

U.S. PATENT DOCUMENTS

| | | | |
|---|---|---|---|
| 2,457,867 | 1/1949 | Chambers | 226/82 |
| 2,573,053 | 10/1951 | Pearlman | 73/49.2 UX |
| 2,610,779 | 9/1952 | Fouse | 226/82 |
| 2,880,610 | 4/1959 | McCoy | 73/49.2 |
| 3,577,696 | 5/1971 | Bock et al. | 53/7 |
| 3,783,576 | 1/1974 | Riesenberg et al. | 53/7 |
| 3,987,664 | 10/1976 | Hass et al. | 73/49.2 |

FOREIGN PATENT DOCUMENTS

| | | | |
|---|---|---|---|
| 656,216 | 10/1961 | Italy | 73/45.5 |
| 115,121 | 5/1918 | United Kingdom | 73/45.5 |

Primary Examiner—Richard C. Queisser
Assistant Examiner—Joseph W. Roskos

[57] ABSTRACT

Container pressure testing apparatus includes a housing having an open portion for sealably engaging the container surface circumscribing a pour opening of the container. Pressurized air is issued from the housing through the pour opening into the container and, on preselected container pressurization, a closure member for the pour opening is displaced within the housing in the direction of the pour opening. On the occurrence of predetermined pressure-induced force on the enclosure member, the closure member is rotated into securement with the pour opening.

8 Claims, 5 Drawing Figures

APPARATUS FOR PRESSURE TESTING OF CONTAINERS

FIELD OF THE INVENTION

This invention relates to apparatus for testing containers and more particularly to apparatus for pressure testing shipping drums and the like.

BACKGROUND OF THE INVENTION

Conventional testing practices in the drum and pail container industry provide for assurance of leak-proof quality of container bodies, bottoms and head double seam. On the other hand, these known practices fail to enable examination of leak-proof quality in respect of the container head end where the testing involves the admission of pressurized air through a head end pour opening. In this omission, current testing practices fail in providing evidently desirable complete container quality data at the point of container manufacture. A still further disadvantage of known testing practices is their inability to provide continuity in monitoring container defects or quality deterioration occurring with passage of extended periods of time, e.g., the time extending from testing to use, or throughout shipment thereof to use.

SUMMARY OF THE INVENTION

It is an object of the present invention to provide for improved container testing and apparatus therefor.

It is a more specific object of the invention to provide apparatus for internal air pressurization and sealing of shipping drums having a pour opening in the head end thereof.

In attaining the foregoing and other objects, the invention provides apparatus including a housing having an open portion for sealably engaging the container surface circumscribing a pour opening of the container. Pressurized air is issued from the housing through the pour opening into the container and, on preselected container pressurization, a closure member for the pour opening is displaced within the housing in the direction of pour opening. On the occurrence of predetermined pressure-induced force on the enclosure member, the closure member is rotated into securement with the pour opening.

The above and other features of the invention will be further understood from the following detailed description of a preferred embodiment of apparatus according with the invention and from the drawings wherein like reference numerals identify like parts throughout.

DESCRIPTION OF THE PREFERRED EMBODIMENT

Figure 1:
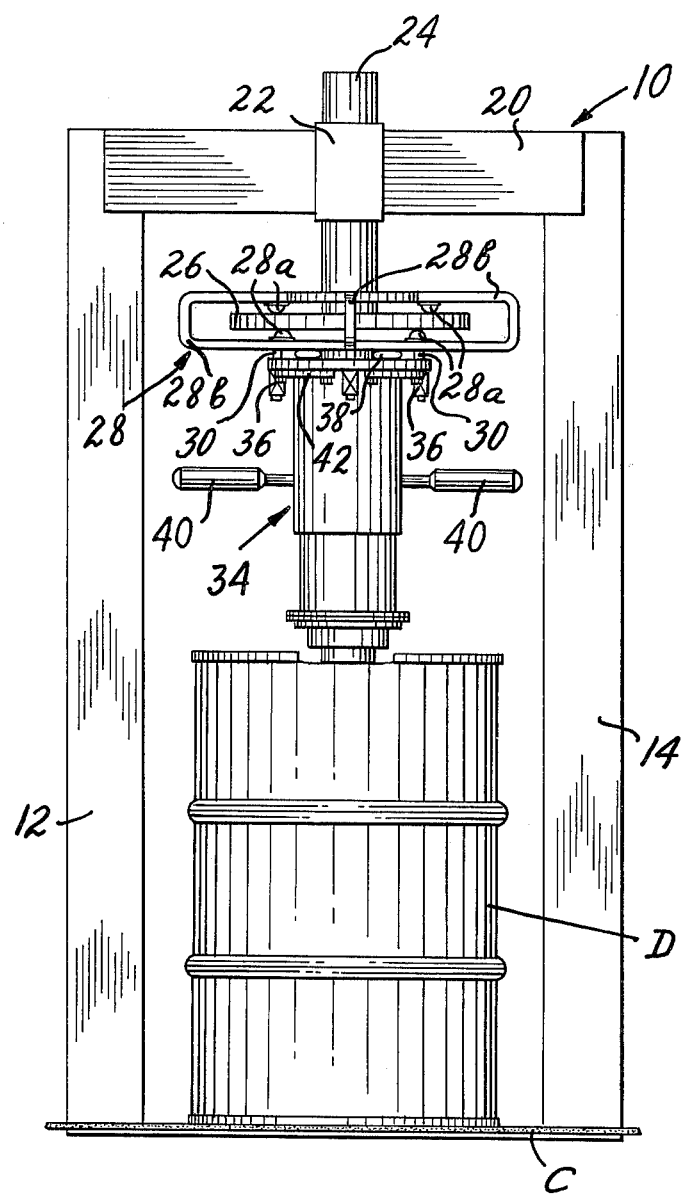
FIG. 1 is a front elevation of apparatus of the invention in operative testing relation to a drum.
Figure 2:
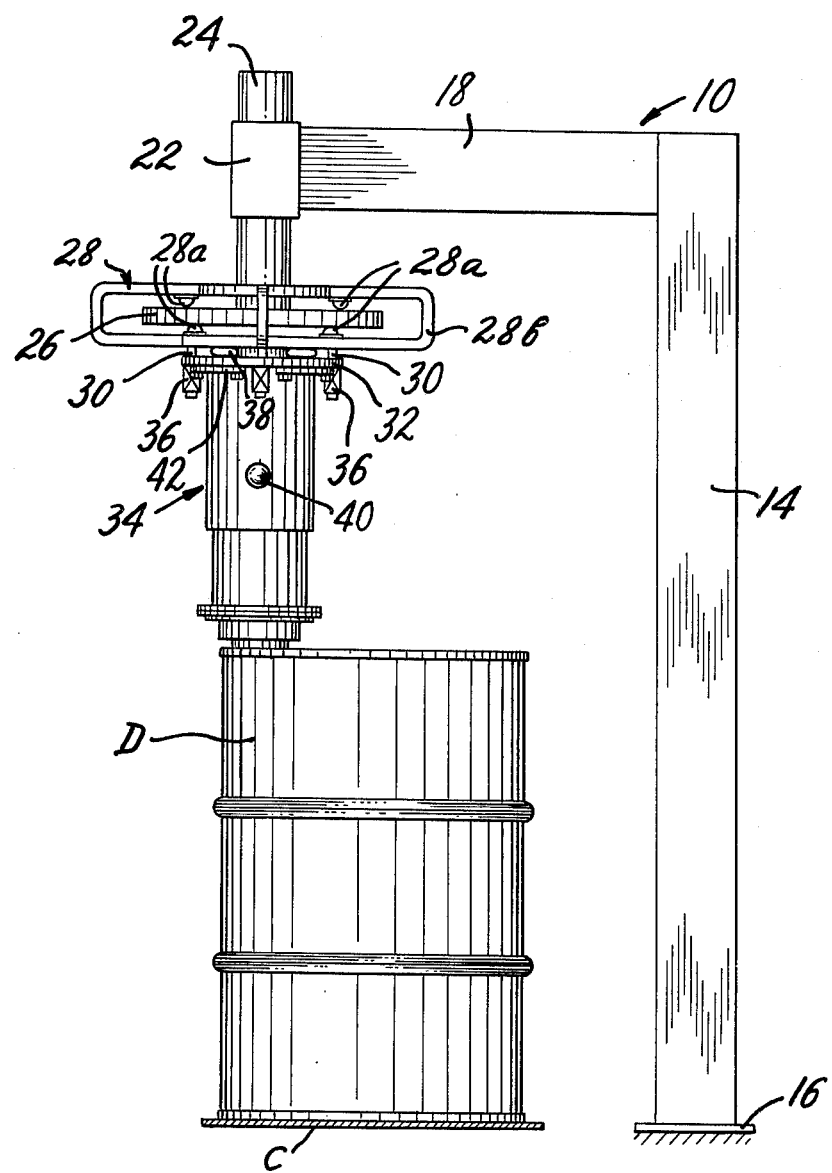
FIG. 2 is a side elevation of the FIG. 1 arrangement.

Referring to FIGS. 1 and 2, the container testing apparatus therein includes an overhanging support frame 10 having side struts 12 and 14 secured to a base 16. Arms 18 are secured to struts 12 and 14 and support a beam 20 forwardly of the struts. Collar 22 is supported by beam 20 and in turn supports shaft 24. At its downward end, shaft 24 disposes bearing plate 26 in horizontal attitude.

Cross-shaped open frame 28 includes slide bearings 28a engaging vertically opposite surfaces of plate 26 whereby frame 28 may be displaced universally horizontally in measure limited by abutment of plate 26 with the vertical end members 28b of frame 28.

Support pins 30 are fixedly secured to and depend downwardly from frame 28. The pins extend through apertures (not shown) in top plate 32 of test head 34. Compression spring units 36 are secured to the ends of pins 30 downwardly of plate 32. Expandable air tube 38 is interposed between frame 28 and plate 32 whereby, on pressurization of tube 38, test head 34 may be displaced downwardly against the opposing restraint of spring units 30, such condition being shown in FIG. 1.

To facilitate the above-noted universal horizontal movement of frame 28 and hence the registration of test head 34 with the pour opening of drum D on conveyor C, the test head includes handles 40.

Figure 3:
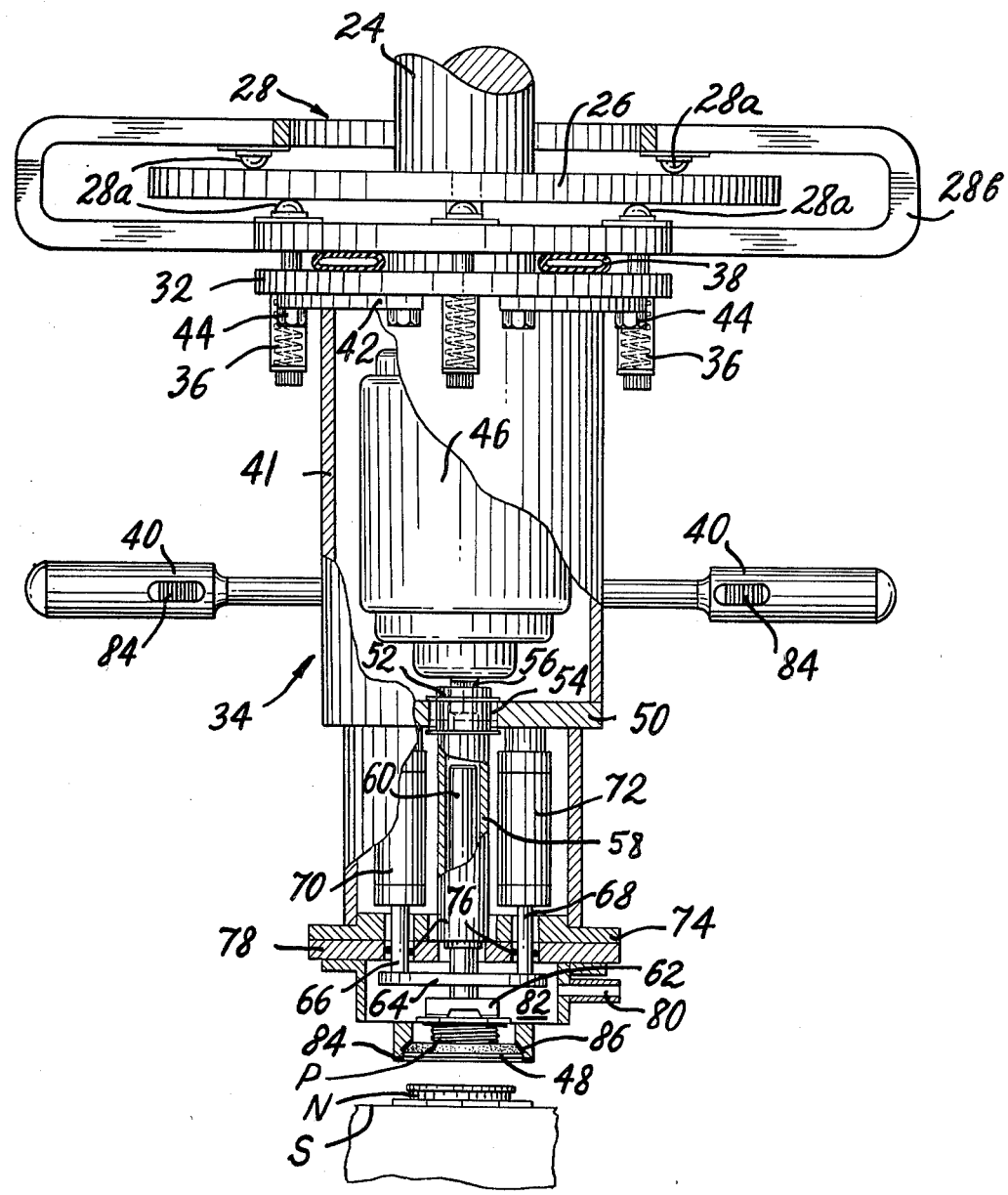
FIG. 3 is a front elevation of the FIG. 1 apparatus broken away in part to show interior detail and further depicting the apparatus in retracted position from the pour opening of the FIG. 1 drum.

Referring now to FIG. 3, tube 38 is shown unpressurized and test head 34 is biased by spring units 30 into its retracted position wherein the test head is vertically upward of neck N of the drum pour opening extending through drum top surface S.

Test head 34 comprises a cylindrical housing 41 depending from flange 42, the flange being secured to plate 32 by nuts 44. Housing 40 has an upper portion containing air motor 46 and extends below such upper portion to a lowermost portion terminating in open end 48. Intermediate such portions, the housing includes an upper transverse member 50 which supports coupling 52 in bearing 54. Coupling 52 receives motor shaft 56 and transmits its rotational output to tubular shaft 58. Shaft 58 is coupled interiorly to spline shaft 60. At its lower end, spline shaft 60 has magnetic plug wrench 62 secured thereto. Shaft 60 is rotatively fixed, above wrench 62, to actuator bar 64 of an actuator unit also comprising piston shafts 66 and 68 and air cylinders 70 and 72. The cylinders are fixed to transverse member 50 and piston shafts 66 and 68 extend freely through further transverse member 74 and sealably, per O-rings 76, through plate 78 which is releasably secured to member 74 for apparatus change noted below. Air pressurization conduit 80 is accessible exteriorly of housing 34 and extends into housing cavity 82. Cavity 82 circumscribes wrench 62 and is in fluid pressure communication with housing open end 48.

In use of the disclosed apparatus, a metal closure member for drum D, shown as plug P in FIG. 3, is applied to wrench 62 to be releasably retained thereby for ultimate securement to neck N of the drum pour opening. Air cylinders 70 and 72 are connected by fittings thereon through a common control valve V3 (FIG. 4) to pressurized air. Conduit 80 is connected through an on-off valve V2 (FIG. 4) to pressurized air. Expandable tube 38 is connected to pressurized air through a valve V1 (FIG. 4) operated responsively to switches 84 on handles 40. With such connections made, a drum is conveyed into general registry with head 34 and an operator displaces the head by horizontal movement of handles 40 until end opening 48 is precisely above neck N of the drum.

On completion of such alignment phase, any one of switches 84 is operated. On this occurrence, tube 38 is pressurized and head 34 descends, bringing end portion 48 into sealed engagement with surface S of the drum. Pressurized air flows at this time through conduit 80, cavity 82 and neck N into the interior of drum D. On the occurrence of a preselected pressure level in cavity 82, occasioned by desired pressurization of the drum interior, valve V3 common to cylinders 70 and 72 of the actutor assembly is operated, in turn moving piston shafts 66 and 68, actuator bar 64 and spline shaft 60 and translating wrench 62 downwardly. Such preselected pressure is sensed by pressure switch PS-1 (FIG. 4), which is arranged to sense pressure level in conduit 80.

As the closure member releasably retained by wrench 62 approaches mating relation with drum neck N, the pressurized air in the drum interior exerts increased closure-opposing force on the closure member and hence on the elements of the actuator assembly, particularly evidenced by increased pressurization level in cylinders 70 and 72. On the occurrence of predetermined increase in pressure within the cylinders, a pressure switch PS-2 (FIG. 4) in the supply line to the cylinders is closed energizing air motor valve V4 (FIG. 4), affecting threading securement of the closure member and neck N.

The impact wrench assembly, inclusive of motor 46, coupler 52, spline shafts 58 and 60 and magnetic wrench 62 is a variable-length rotational drive assembly and is set to a predetermined torque setting to insure that the securement of closure member and pour opening neck is sufficiently tight to maintain air tightness.

The configuration of neck N in FIG. 3 is that of so-called "trisure" opening and housing end portion 48 is configured accordingly with a flat horizontally disposed seal 84 and a further seal 86 inwardly of seal 84 and acutely arranged as indicated. Where drums being processed in accordance with the invention have so-called "rieke" openings, plate 78 and elements downwardly depending therefrom in FIG. 3 are removed, as permitted by the above-noted releasable securement of plate 78 and member 74, and a substitute assembly adapted for the rieke opening is installed. The end portion of the housing thereupon presents suitable sealing constituents for the rieke opening, comprising a single horizontal end seal having a suitable tapered radially interior opening.

Figure 4:
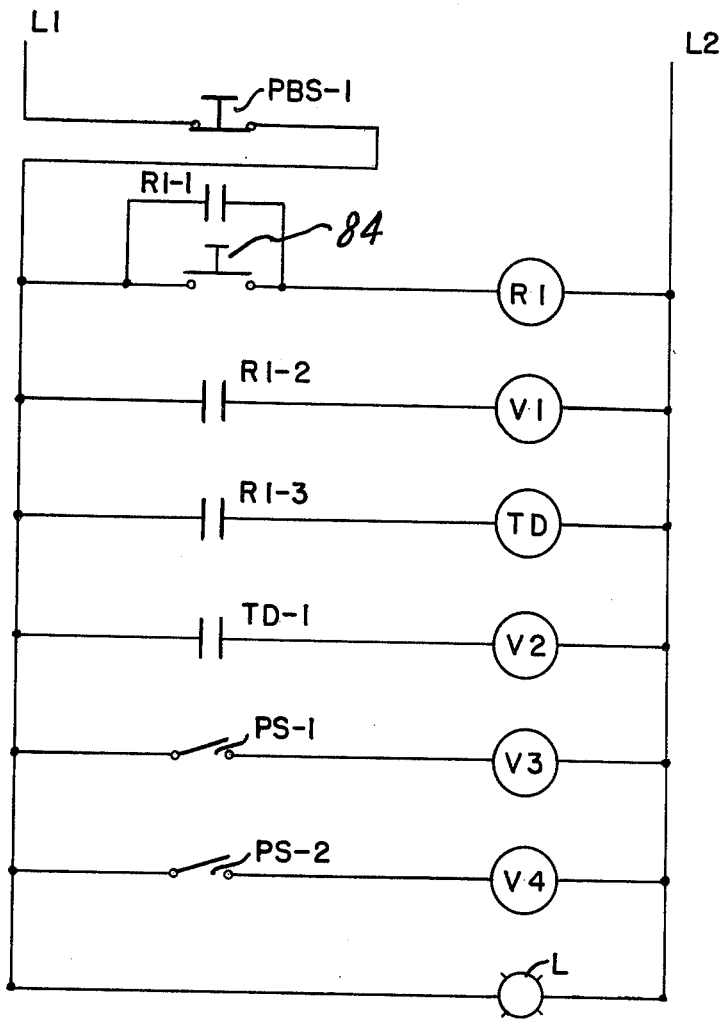
FIG. 4 is an electrical schematic diagram of control circuitry of the invention.

Referring to FIG. 4, lines $L_1$ and $L_2$ are fed from a single phase, 115 volt, 60 cycle supply and are suitably fused. System on-off push buttom switch PBS-1 is normally closed as indicated, and lamp L is energized. On operation of anyone of switches 84, as discussed above, relay R1 is energized, thereupon closing its normally-open contacts R1-1, R1-2 and R1-3. Closure of contacts R1-1 serves to latch relay R1. Closure of contacts R1-2 energizes valve V1, affecting supply of pressurized air to expandable tube 38. Closure of contacts R1-3 connects time delay relay TD across lines $L_1$ and $L_2$ and, on the expiration of a preselected time, established by the time delay relay and sufficient to allow for full descent of the test head into sealed engagement with drum surface S, contacts TD-1 of relay TD are closed. On closure of contacts TD-1, valve V2 is energized and pressurized air is supplied through conduit 80 to the drum interior. Upon the occurrence of pressure level in conduit 80 indicating desired pressurization of the drum interior, pressure switch PS-1 is closed, energizing valve V3 through which air is supplied to air cylinders 70 and 72. As discussed above, in the course of displacement of plug P, pressure switch PS-2 is closed, energizing valve V4 whereupon air motor 46 is energized, threading the plug into the drum pour opening. Operation of PBS-1 resets the FIG. 4 circuitry.

As will be appreciated from the foregoing, the apparatus of the invention enables complete pressurization of the interior of a container, inclusive of sealing the container pour opening. By this practice, the entire exterior surface of the container can be tested by various methods, e.g., water immersion, to determine whether air is escaping from its pressurized interior. Further, containers pressurized and sealed in accordance with the invention may be shipped to consumers with indication of the interior pressure level at the point of testing. Loss of air pressure during transit or consumer storage then readily can be detected and compared with such indication by the consumer at the time of container use. Loss of air pressure will of course indicate an air leakage defect in the container and cause for rejection.

It will thus be seen that testing of containers pressurized in accordance with the invention is a continuing process, and may extend over time periods far in excess of the customary limited time period involved in the actual testing operation at the point of testing. The level of pressurization of containers is evidently dependent on size, configuration, thickness of materials and like container parameters.

Various modifications may be introduced in the foregoing particularly disclosed and preferred embodiment of the test apparatus without departing from the invention. Accordingly, the embodiment above-described and depicted in the drawings is intended in an illustrative and not in a limiting sense. The true spirit and scope of the invention is set forth in the following claims.

What is claimed is:

1. In combination, in apparatus for use in testing leakage in a container having a surface including a pour opening: housing means for sealably engaging said container surface and for issuing pressurized air through said pour opening into said container; means for releasably retaining a closure member and supported for movement in said housing means; actuator means for translating such closure member retaining means toward said pour opening on preselected pressurization of said container and drive means responsive to predetermined pressure-induced force on said closure member in such translation thereof and energizable thereby for imparting further movement to said closure member retaining means to secure said closure member to said pour opening.

2. The invention claimed in claim 1 wherein said drive means comprises air motor means for imparting rotation to said closure member retaining means.

3. The invention claimed in claim 2 wherein said closure member retaining means includes an end member for engaging said closure member and wherein said drive means includes a variable length linkage connecting said motor and said closure member retaining means.

4. The invention claimed in claim 3 wherein said actuator means includes output means translated on said preselected pressurization of said container, said output means being secured to said closure member retaining means and extending said variable length linkage of said drive means.

5. The invention claimed in claim 4 wherein said actuator means comprises air cylinder means, said combination further including transducer means responsive to air pressure change in said air cylinder means according with occurrence of said predetermined pressure-induced force on said closure member for energizing said drive means.

6. The invention claimed in claim 3 wherein said variable-length linkage comprises a splined shaft assembly having one shaft driven by said air motor means and a second shaft secured to said closure member.

7. The invention claimed in claim 1 further comprising means for supporting said housing for universal movement parallel to said container surface of prescribed measure to enable registration of said housing with said pour opening and for movement of said housing transverse to said container surface to affect such sealable engagement of said housing with said container surface.

8. Apparatus for use in testing leakage in a container of type having a surface including a pour opening comprising:

(a) means for releasably retaining a closure member for said pour opening and activatable to secure said closure member to said pour opening;
(b) housing means having an open end portion for sealably engaging said surface of said container, said housing means defining a cavity opening into said end portion and circumscribing such closure member retaining means and having air pressure conduit means communicating with said cavity and accessible exteriorly of said housing means;
(c) actuator means operative on preselected pressurization of said cavity to move said closure member retaining means toward said housing means open end portion; and
(d) drive means responsive to predetermined pressure-induced force on said closure member to operate said closure member retaining means to affect such securement of said closure member to said pour opening.

* * * * *